(12) United States Patent
Cursiefen et al.

(10) Patent No.: US 11,931,242 B2
(45) Date of Patent: Mar. 19, 2024

(54) DEVICE FOR THE PREPARATION OF A DESCEMET'S MEMBRANE-ENDOTHELIUM GRAFT

(71) Applicant: Universitaet Zu Koeln, Cologne (DE)

(72) Inventors: Claus Cursiefen, Cologne (DE); Bjoern Bachmann, Cologne (DE); Sebastian Siebelmann, Solingen (DE)

(73) Assignee: UNIVERSITAET ZU KOELN, Cologne (DE)

( * ) Notice: Subject to any disclaimer, the term of this patent is extended or adjusted under 35 U.S.C. 154(b) by 139 days.

(21) Appl. No.: 17/635,257

(22) PCT Filed: Aug. 13, 2020

(86) PCT No.: PCT/EP2020/072701
§ 371 (c)(1),
(2) Date: Feb. 14, 2022

(87) PCT Pub. No.: WO2021/032575
PCT Pub. Date: Feb. 25, 2021

(65) Prior Publication Data
US 2022/0287821 A1    Sep. 15, 2022

(30) Foreign Application Priority Data
Aug. 16, 2019    (EP) .................... 19192064

(51) Int. Cl.
*A61F 2/14*    (2006.01)
*A61F 9/007*    (2006.01)

(52) U.S. Cl.
CPC .......... *A61F 2/148* (2013.01); *A61F 9/00781* (2013.01)

(58) Field of Classification Search
CPC ......... A61F 2/148; A61F 2/1691; A61F 9/007
See application file for complete search history.

(56) References Cited

U.S. PATENT DOCUMENTS

| 2005/0125000 A1* | 6/2005 | Tourrette | ............... A61F 2/1678 606/107 |
| 2006/0200167 A1* | 9/2006 | Peterson | ............... A61F 2/1678 606/107 |
| 2008/0269769 A1 | 10/2008 | Dybbs | |

(Continued)

FOREIGN PATENT DOCUMENTS

| DE | 10 2016 104 680 A1 | 9/2017 |
| EP | 3 705 089 A1 | 9/2020 |
| WO | 2011/102725 A1 | 8/2011 |

*Primary Examiner* — Sarah W Aleman
(74) *Attorney, Agent, or Firm* — Norris McLaughlin, P.A.

(57) ABSTRACT

A device for the preparation of a Descemet's membrane-endothelium graft includes a bowl with an inner bottom and a sidewall surrounding the bottom, particularly the bowl being configured to receive a fluid and a Descemet's membrane-endothelium graft or a donor cornea graft comprising a Descemet's membrane-endothelium graft floating in the fluid, a preparation area positioned in a first part of the inner bottom of the bowl, particularly for receiving and preparing the graft prior to transport, a transfer area positioned in a second part of the inner bottom between the preparation area and an outlet opening in the sidewall, particularly the opening being entirely positioned below the upper rim of the sidewall.

21 Claims, 8 Drawing Sheets

(56) References Cited

U.S. PATENT DOCUMENTS

| | | | |
|---|---|---|---|
| 2009/0270982 A1* | 10/2009 | Torres | A61F 2/0095 206/363 |
| 2012/0226286 A1* | 9/2012 | Weston | A61F 2/0095 606/107 |
| 2015/0150242 A1* | 6/2015 | Busin | A61F 2/1691 435/284.1 |
| 2022/0151766 A1 | 5/2022 | Bachmann et al. | |

* cited by examiner

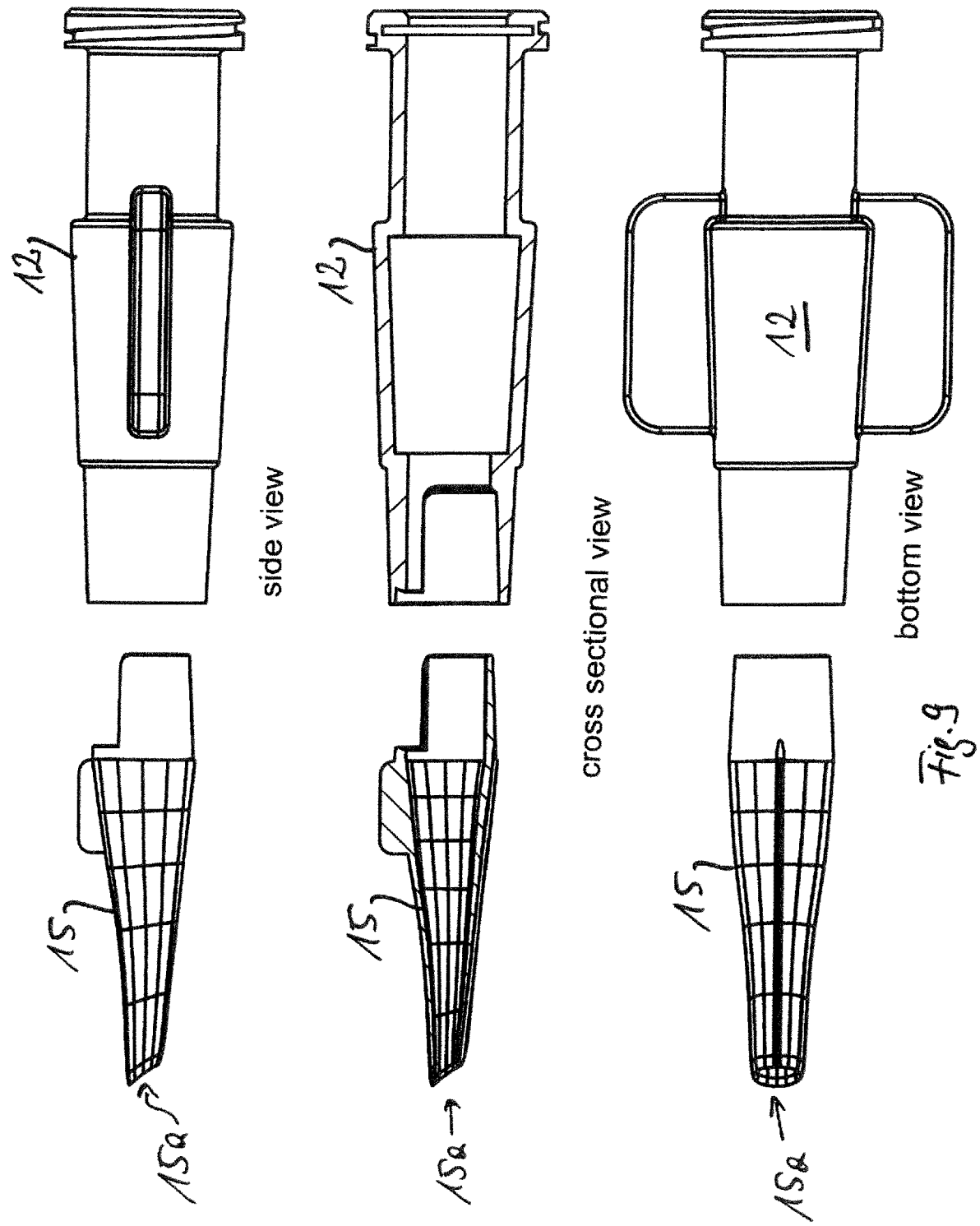

DEVICE FOR THE PREPARATION OF A DESCEMET'S MEMBRANE-ENDOTHELIUM GRAFT

The invention relates to a device for the preparation of a Descemet's membrane-endothelium graft.

An eye surgery referred to as DMEK is well known in the state of the art. This kind of surgery is used in order to insert the Descemet's membrane with endothelium originating from a donor eye into a recipient eye, after its affected Descemet's membrane has been removed.

For this purpose a donor cornea is prepared by removing the Descemet's membrane-endothelium from it to form a graft. This is typically done in a first preparation device. The extracted Descemet's membrane-endothelium graft needs to be transferred at least once into another second device, for example for further handling during the surgery. Another transfer may be necessary if a graft needs to be transported or stored for a longer time. Any transfer between devices performed with tools is very problematic since the graft is very sensitive and may be easily harmed by contact with any kind of tool or device.

Accordingly, it is an object of the invention to provide a device for the preparation of a Descemet's membrane-endothelium graft that helps to reduce the number of contacts of the graft with other tools or devices on its way to surgery.

This object is solved by means of a device for the preparation of a Descemet's membrane-endothelium graft comprising a bowl with an inner bottom and a sidewall surrounding the bottom, a preparation area positioned in a first part of the inner bottom of the bowl and a transfer area positioned in a second part of the inner bottom between the preparation area and an outlet opening in the sidewall.

The inner bottom of the bowl is divided into at least two parts, wherein one part serves to prepare the graft and the second part helps to transfer the prepared graft into a transport device.

Preferably the bowl is configured to receive a fluid and a Descemet's membrane-endothelium graft or a donor cornea graft comprising a Descemet's membrane-endothelium graft floating in the fluid, preferably the fluid being a liquid, most preferred water or at least a liquid comprising water. Such configuration may be achieved by means of the inner volume of the bowl, that serves to receive a fluid, preferably the fluid containing water and the graft.

The preparation area is particularly configured for receiving and preparing the graft prior to transportation. For example for this purpose the preparation area forms the lowest part of the inner bottom in the bowl, preferably at least in a first position of the bowl for preparing the graft. The bowl may be positioned in other different positions, at least in a second position for the purpose of transferring the prepared graft to a transport device. In a second position the bowl may be rotated by an angle around a horizontal axis, this rotation and/or second position causing the fluid to flow towards the outlet opening, particularly by reducing the height of the outlet opening, particularly in an external frame of reference. The invention may provide that the bowl can stand in a stable fashion on a support (table or the like) in at least the first position, preferably in the first and second position.

Providing the preparation area in the lowest part of the inner bottom leads to the advantage that a floating graft automatically will position itself in that area by gravity. Furthermore manually moving the bowl will facilitate to position the graft in that area. Alternatively the graft may be easily handled in the floating state with a tool without the risk of harmful contacts.

After successful preparation of the graft in the preparation area a simple moving of the bowl will cause a fluid flow in the bowl according to the movement which can be used to transfer the graft together with this flow through the transfer area of the bowl towards the outlet opening.

The opening is preferably totally encircled be the sidewall, particularly the opening is entirely positioned below the upper rim of the sidewall. This provides the advantage that the fluid flowing through the transfer area to the outlet opening and through the outlet opening may carry the prepared graft on its way into the transport device that may be positioned behind the opening, regarded in the direction of flow. The transport device may be fixed to the opening—for example by means of a connector—to assure that the fluid carrying the graft will definitely be received in the transport device.

It is clearly understood that using this bowl shaped device leads to the advantage that no additional tool needs to be used to transfer the prepared graft into the transport device for further handling the graft, for example for transporting the graft in the device to the site of surgery or even to store the graft in the device for a longer time. Preferably, the transport device is also configured to be connected to an applicator and to eject the graft out of this transport device into and through the applicator into the eye during a surgery. For this purpose the transport device may be attached to the applicator with the same connecting element (for example Luer-Lock) that was used before for connecting the transport device to the connector of the bowl. Accordingly, no additional tool contact is needed. The bowl, transport device and the applicator may form a set or kit in order to be used together. All parts of such set being configured to co-work, particularly to get connected to the corresponding counterpart.

The applicator may comprise a tube to which the transport device is attached at the distal end of the tube. The proximal end of the applicator-tube that faces the eye during surgery is configured to be insertable into the anterior eye chamber. The tube may preferably comprise a guiding element that helps to guide and preferably to unfold the graft, if this is wound up. The guiding element may preferably extend out of the tube and beyond the proximal opening of the tube. Accordingly, the guiding element may also be introduced into the anterior eye chamber.

Preferably, any kind of contact with the graft is done indirectly via the fluid carrying the graft.

In a preferred embodiment of the bowl the preparation area comprises a recess, the inner surface of the recess being positioned below an area of the inner bottom surrounding the recess. Accordingly, this recess will form the lowest part of the inner volume of the bowl. The recess is preferably adapted to receive an entire donor cornea. For example the diameter of the recess is smaller than 3 times the diameter of the donor cornea, preferably smaller than 2 times the diameter of the donor cornea. In absolute values the diameter of the recess in the plane of the surrounding inner bottom may be smaller than 30 mm, preferably smaller than 20 mm.

In a further improvement the inner surface of the recess may comprise at least one opening, preferably several openings, the at least one opening being in fluid connection with a channel in the bowl for extracting fluid out of the recess. By extracting fluid out of the recess the graft or the cornea may be fixed by suction at the bottom surface of the recess.

Preferably this extracted fluid can be a gas or air. The fluid can be a liquid as well, for example water or at least a liquid containing water.

In a possible method of preparing the graft the wet graft may be put into the recess not yet containing a liquid. By extracting air through the channel that is communicating with the at least one opening in the bottom of the recess the graft is fixed by low pressure. It is also possible that the graft is put into the recess already containing a liquid. In this situation the liquid may be extracted through the channel.

At least the recess of the preparation area may be filled with a liquid and the fixed graft prepared. After preparation the low pressure is released and the prepared graft is free floating in the liquid.

The preparation can be done in a different way as well. Irrespective of the kind of preparation the graft can be transferred towards the outlet opening by causing the liquid to flow towards the opening. This can be caused by tilting the bowl and decreasing the height of the outlet opening. The graft will be carried to the outlet opening and into the attached transport device together with the liquid. The device can now be detached and closed for transportation.

In a preferred embodiment the preparation area, particularly the recess of it may be formed by means of a separate bottom element that may be insertable into the inner bottom and may be removed out of the inner bottom.

The bowl may preferably comprise a hollow chamber underneath the inner bottom and being open towards the inner bottom for receiving this separate bottom element, the channel in the bowl for extracting fluid out of the recess merging into the chamber. Since the chamber preferably has an opening in the plane of the inner bottom that surrounds the chamber the separate bottom element may be inserted into the inner bottom and removed in a vertical direction. Preferably, after insertion the separate element is flush with the surrounding area of the inner bottom. Such a separate bottom element may be used once for the preparation of a graft whereas the remaining bowl may be used several times.

Furthermore preferred the second part of the inner bottom forming the transfer area is increasing in height towards the outlet opening, preferably at least when regarding the bowl in a first position for preparation of the graft.

This ensures, that the prepared graft will not float out of the preparation area through the transport area towards the outlet opening unless the bowl is inclined to an inclined position, preferably the second stable position, causing that the fluid starts floating in the direction of the outlet opening. To get the bowl inclined the bowl may be handled manually.

Preferably the outlet opening in the sidewall leads into a connector to which a transport device is at least temporarily attachable or attached. As mentioned the transport device is preferably configured to receive the prepared graft for transportation purposes by letting the fluid flow and carrying the graft into the transport device through the opening.

Due to the increase in height of second part of the inner bottom forming the transfer area the outlet opening, the connector and/or a connected transport device are positioned higher than the preparation area, particularly at least in a first position of the bowl for preparing the graft.

Preferably, the upper rim of the sidewall surrounding the transfer area is as well increasing in height towards the outlet opening, particularly at least in a first position of the bowl for preparing the graft. The invention may provide, that the height of the sidewall above the inner bottom is constant in any circumferential position of the bowl.

Furthermore the first part of the inner bottom of the bowl may comprise a first plane surface area surrounding the preparation area and the second part of the inner bottom of the bowl may comprise a second plane surface which is a part of the transfer area, the second plane surface area rising in height towards the outlet opening, particularly a least in a first position of the bowl for preparing the graft.

When regarded in a top view the second (particularly plane) surface part of the inner bottom may preferably be tapered towards the outlet opening. This embodiment will help to guide the flow of fluid carrying the graft directly to the outlet opening. The first surface part of the inner bottom may be at least partially formed circular.

In order to facilitate respective stable positions of the bowl during preparation (first position) and transfer (second position) of the graft towards the opening the bowl may comprise a base for placing the bowl on a support, the lower surface/bottom of the base being configured to provide that the bowl can stand on the support in a stable fashion in the first position and in the second position.

For this purpose the base may comprise a plane first lower surface part, particularly underneath the preparation area and a plane second lower surface part, particularly underneath the transfer area, the second lower surface area rising in height in a direction towards the outlet opening.

Furthermore it is possible that the base comprises a first lower surface part, particularly underneath the preparation area and a second lower surface part, particularly underneath the transfer area, wherein each one of the surface parts comprises at least three contact elements for contacting the support, the contact elements of a respective surface part all lying in the same plane. Accordingly, the contact elements of the first part are all positioned in a first plane and the contact elements of the second part are all positioned in a second plane, the first and second plane being different.

Particularly in the first stable position the plane first lower surface or the first plane of the contact elements is parallel to the upper surface of the support and the second plane surface or the second plane of the contact elements is inclined, preferably rising towards the outlet opening.

In the second stable position vice versa the plane second lower surface or the second plane of the contact elements is parallel to the upper surface of the support and the first plane surface or the first plane of the contact elements is inclined, preferably rising in height.

The contact elements of a respective lower surface part are preferably forming a tripod if three contact elements are provided or a multipod if more than three are provided. Each tripod/multipod provides that the bowl can stand in a stable fashion.

Accordingly, in a first position for preparing a graft the bowl can be placed on a support (e.g. table) with the plane first lower surface part or the contact elements of the first surface part contacting the support and in a second position for transferring the graft towards the outlet opening the bowl can be placed on a support with the plane second lower surface part or the contact elements of the second surface part contacting the support. In the second position the outlet opening has a lower height above the table compared to the first position.

To facilitate a manual preparation the device of the invention may comprise an annular or frame shaped wrist support in addition to the bowl, particularly the wrist support forming a ring or frame being open in a single circumferential position. The bowl can be placed at least in a first position for preparing a graft into the wrist support.

A preferred embodiment of the invention is shown in several figures and will be describe commonly for all figures hereinafter.

Figure 3A:
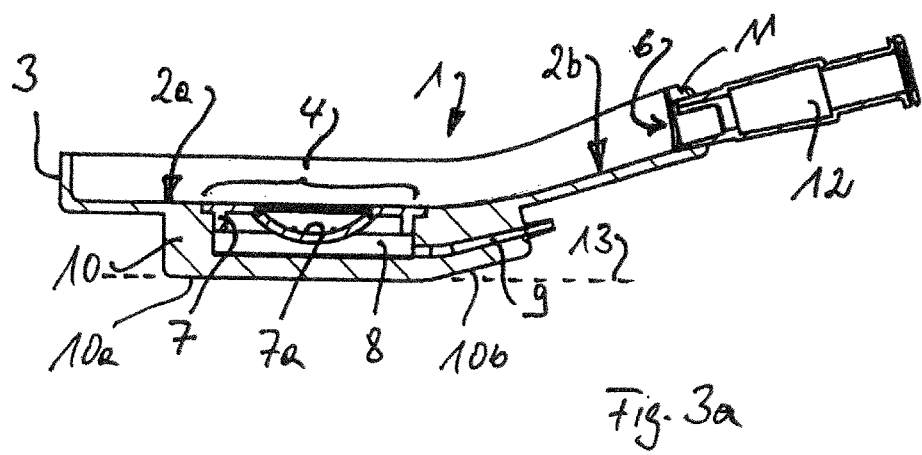
Figure 3B:
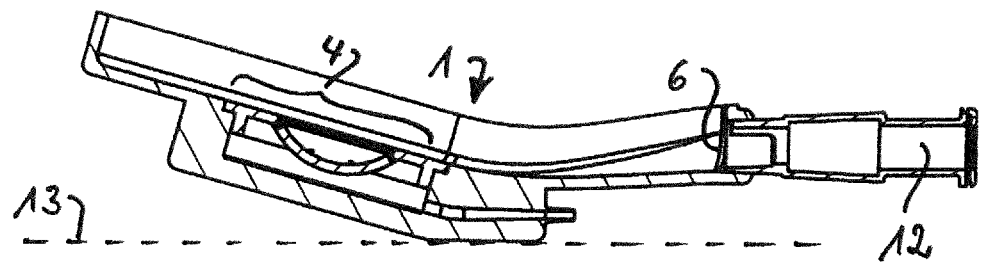
Figure 4:
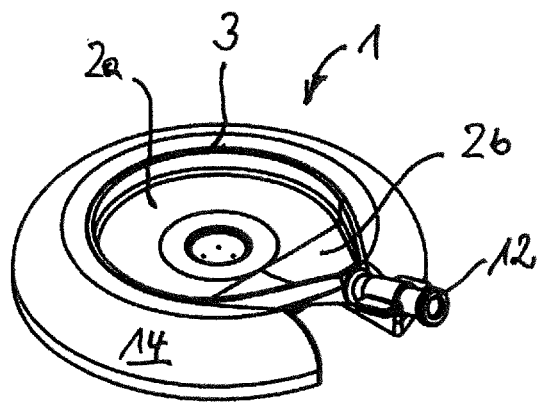
Figure 5:
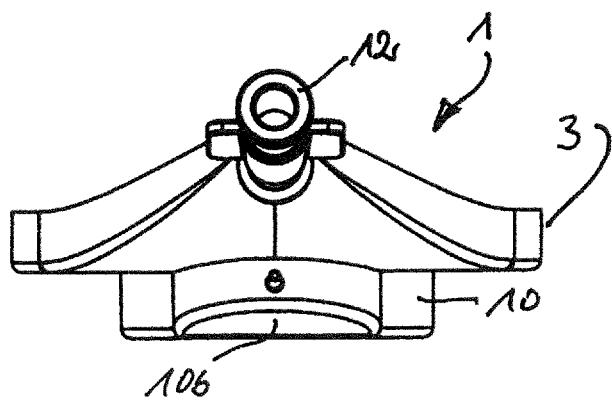
Figure 5A:
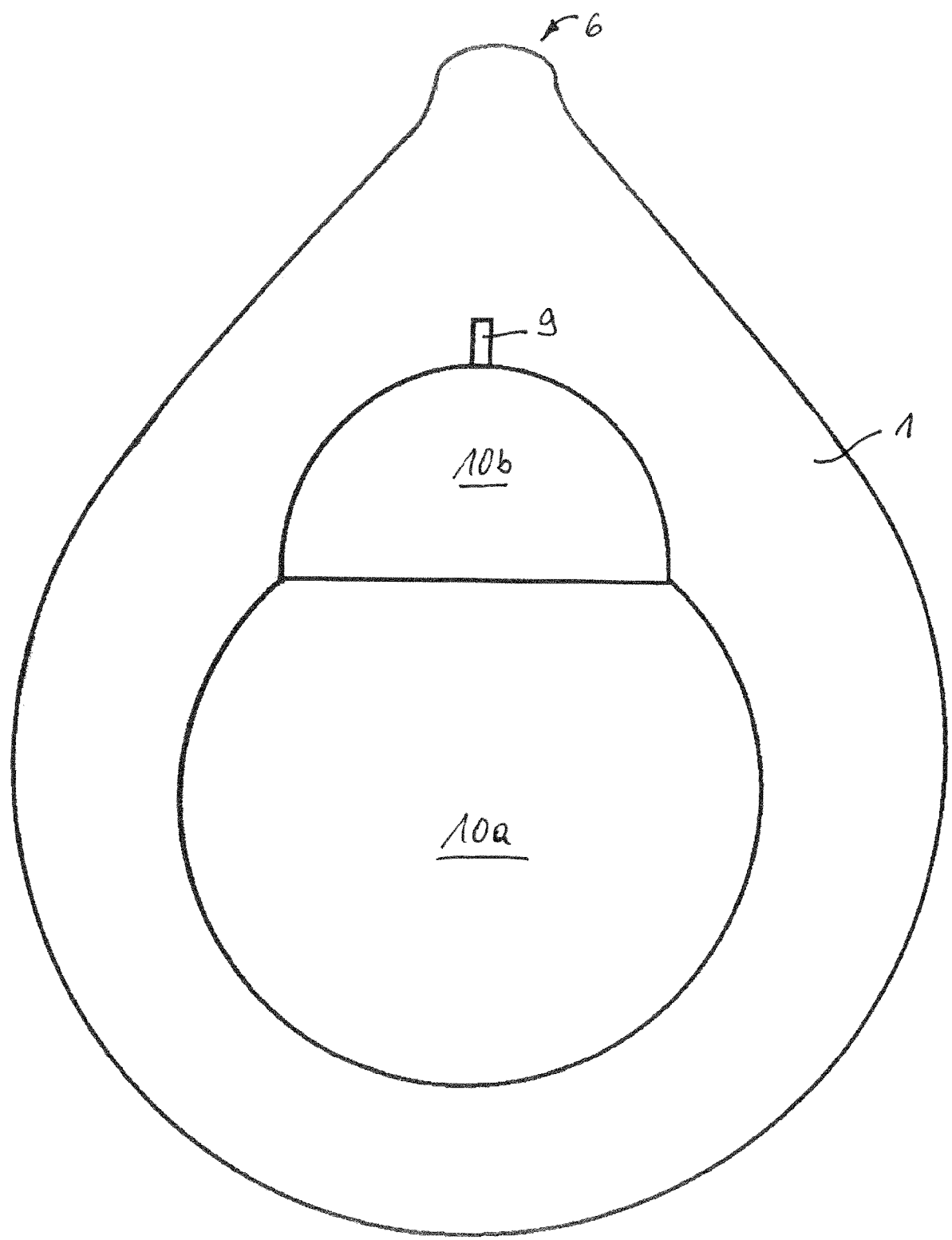
Figure 5B:
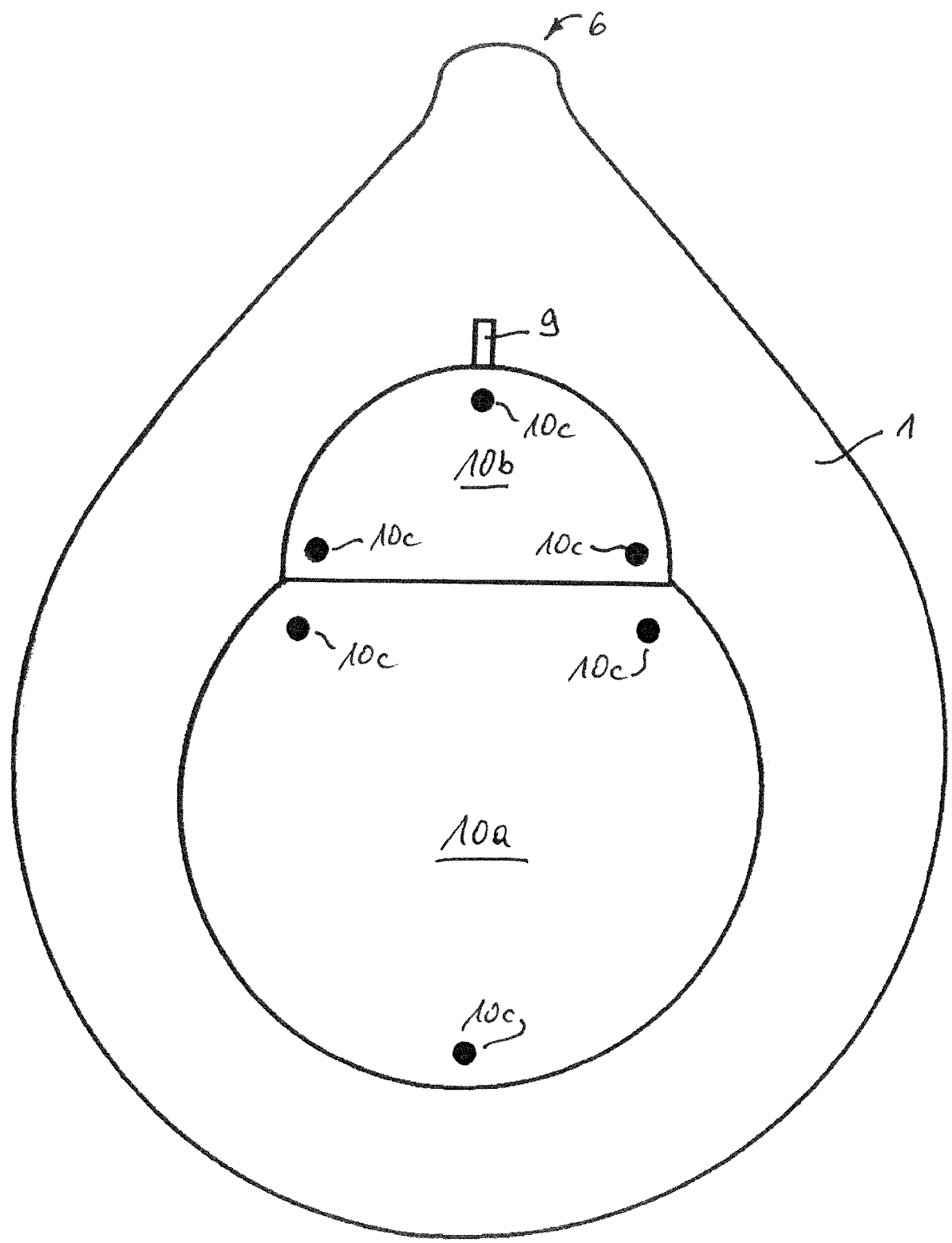
Figure 6:
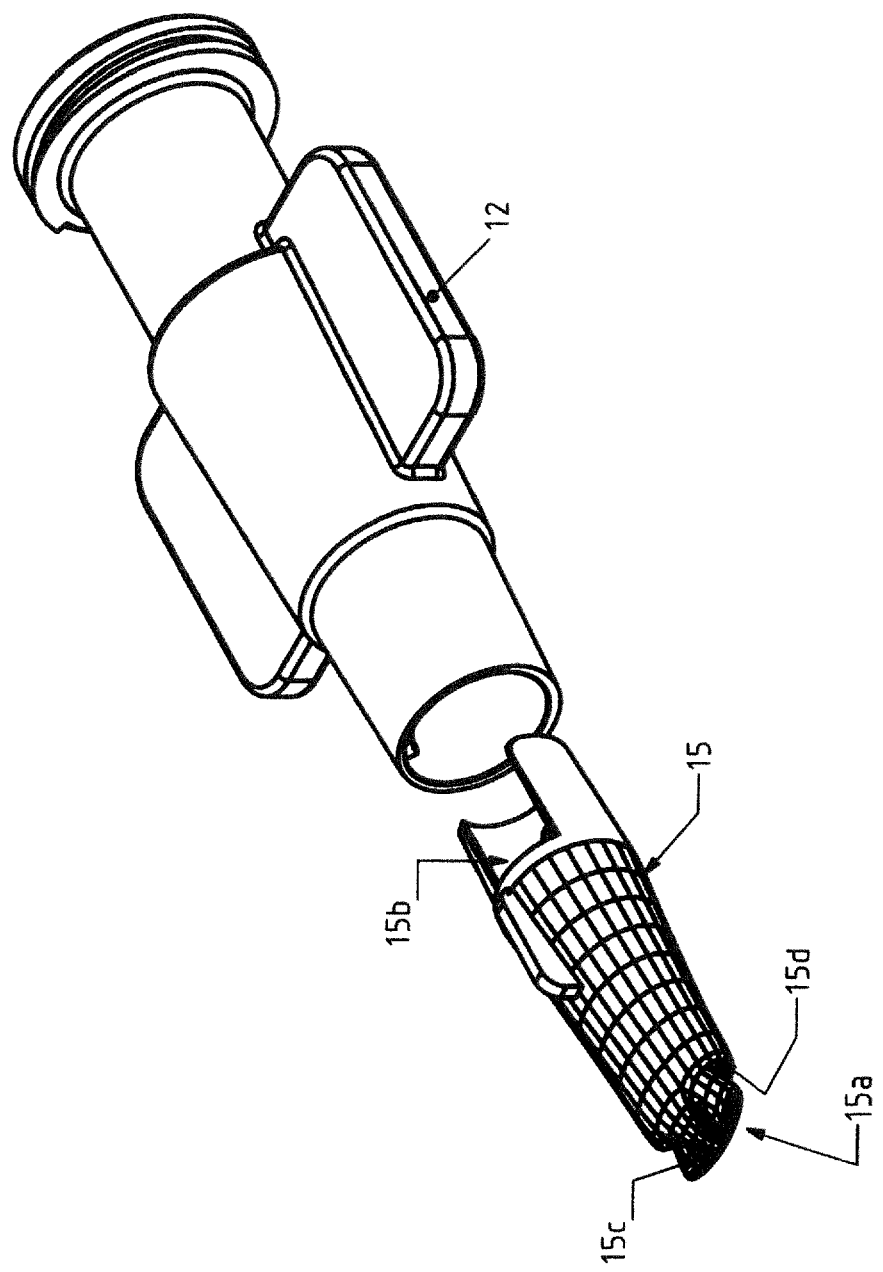
Figure 7:
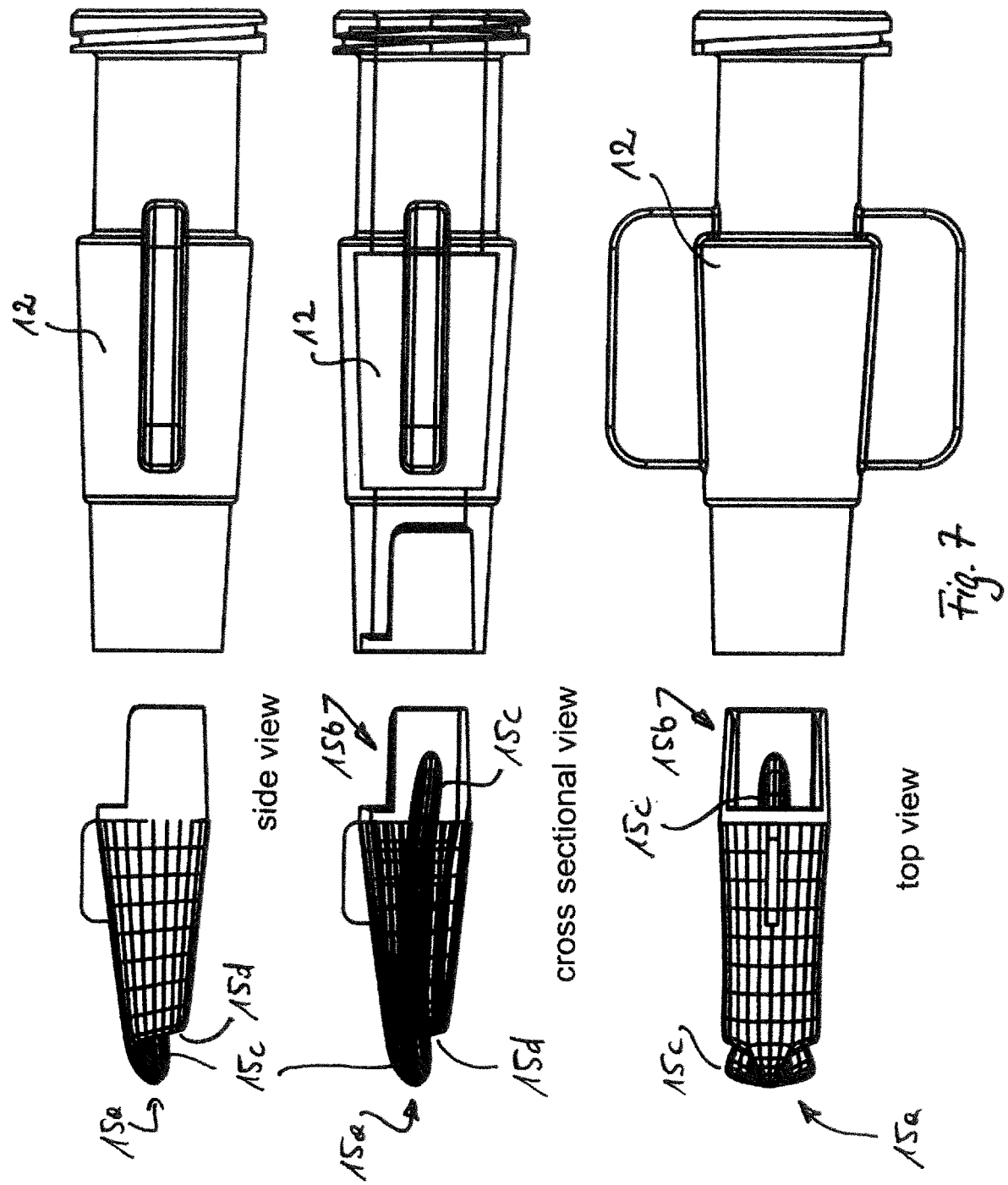
Figure 8:
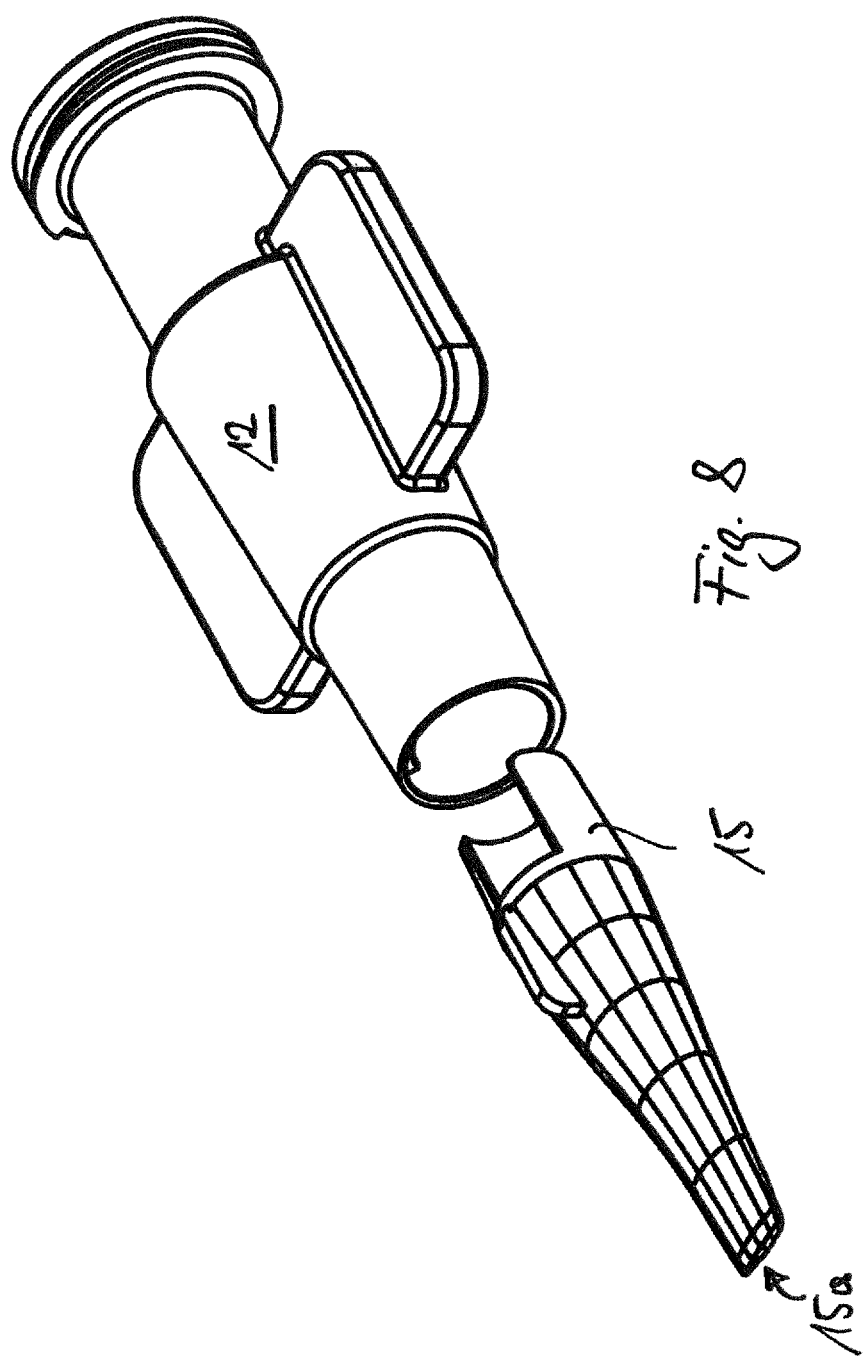

FIG. 3a shows a cross sectional view along line B-B of the bowl in a first stable position standing on a horizontal table FIG. 3b shows a cross sectional view along line B-B of the bowl in a second stable tilted position standing on a horizontal table FIG. 4 shows an isometric view with a wrist support FIG. 5 shows a front view FIG. 5A shows a bottom view with plane lower surface parts of the base FIG. 5B shows a bottom view with tripods in the respective lower parts of the base FIG. 6 shows in a perspective view the possibility to attach the transport device to a first kind of applicator for surgery FIG. 7 shows the transport device and the first kind of applicator in different views FIG. 8 shows in a perspective view the possibility to attach the transport device to a second kind of applicator for surgery FIG. 9 shows the transport device and the second kind of applicator in different views.

All figures show a device of the invention comprising a bowl 1. The bowl is formed by the inner bottom 2 and the sidewall 3 entirely surrounding the bottom 2 at its circumferential periphery. The bottom 2 is subdivided into a first part 2a and a second part 2b. The first part 2a comprises a preparation area 4. The second part 2b together with the respective part of the sidewall 3 form the transfer area 5 that is situated between the preparation area 4 and the outlet opening 6.

In this embodiment the preparation area is formed by a separate element 7 that comprises a recess 7a being the lowest part of the inner volume of the bowl in the shown position, particularly in a first stable position of two different stable positions. In particular in all possible embodiments the preparation area is an area in the bowl comprising the lowest part of the bowl in the first position. The separate element 7 is inserted into a chamber 8 of the bowl 1 that furthermore provides a fluid connection between the channel 9 in the base 10 of the bowl and the opening 7b in the recess 7a by attaching a pump or a syringe to the channel 9 a fluid may be extracted from the recess. The fluid may be air and the graft be fixed by suction. The graft may also be floating in the recess 7a in a liquid and may also be fixed in it by suction.

Figure 1:
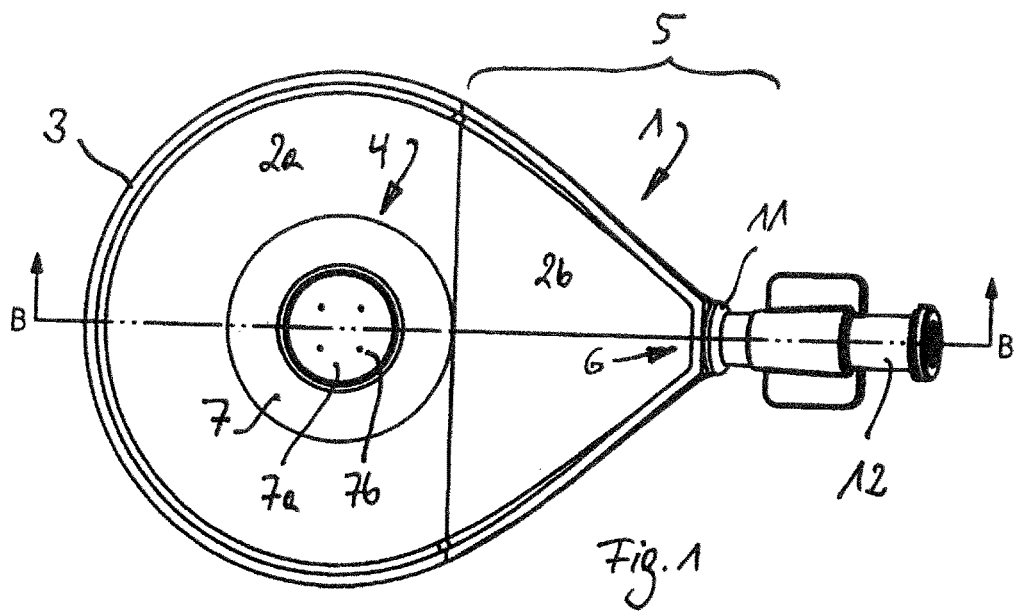
FIG. 1 shows a top view of the device.
Figure 2:
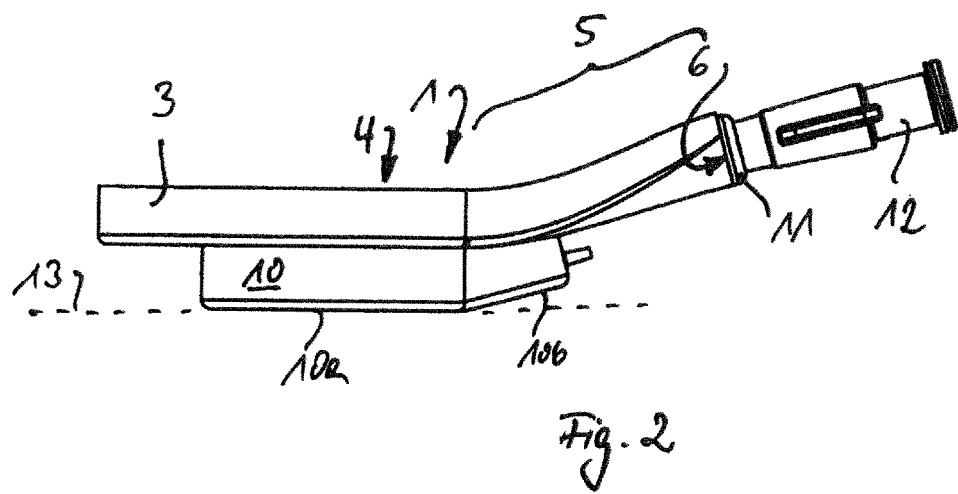
FIG. 2 shows a side view of the device.

FIGS. 2 and 3a/b depict that the transfer area 5, particularly the second part 2b of the inner bottom 2 is increasing in height towards the outlet opening 6, particularly at least in the shown first position in FIG. 3a of two different positions, the second position being shown in FIG. 3b. The top view of FIG. 1 furthermore depicts that the second part 2b is tapered towards the outlet opening 6 thus forming of funnel leading into the opening 6.

The sidewall 3 at the position of the opening 6 comprises a connector 11 to which a transport device 12 is releasable attached.

FIGS. 2 and 3a/b furthermore show that the base 10 of the bowl 1 has a first plane lower surface 10a. This first lower surface 10a is used to place the bowl 1 on a supporting surface 13, for example a horizontal table in a first stable position in which the bowl 1 is used for preparing a graft in the preparation area 4. This first position is shown in the FIGS. 1, 2, 3a, 4 and 5.

The base 10 furthermore has a second plane lower surface 10b. This second lower surface 10b is used to place the bowl on a supporting surface 13 in a second stable position in which the bowl is used to transfer the graft towards the outlet opening 6.

This second stable position of the bowl is shown in FIG. 3b.

Instead of first and second plane lower surfaces the respective lower surface may have contact elements, preferably at least three, the contact elements of a respective lower surface all being in the same plane. An embodiment showing the respective plane lowers surfaces 10a/10b of the base 10 is shown in the FIG. 5A. An alternative embodiment in which the respective lower parts 10a and 10b of the base 10 each comprises three contact elements 10c forming a respective tripod is shown in FIG. 5B.

Inclining the bowl from the first to the second position automatically decreases the height of the opening 6 above the support surface 13 and leads to a flow of the liquid in the bowl 1 towards the opening 6 that is carrying the prepared graft also towards the opening 6 and into the transport device 12. Both positions in the FIGS. 3a and 3b are stable positions of the bowl 1 on the supporting surface 13 due to the fact that the center of gravity of the liquid filled bowl 1 is moving by inclining the bowl 1 from a position above lower surface 10a to a position above lower surface 10b of the base 10.

This transfer can be done entirely without an additional tool what is the big advantage of this device over the state of the art. This transfer can also be done by using a tool for gently pushing the graft floating in the liquid. The transfer can also be done by drawing the liquid into the transfer device using the transfer device.

The height of the sidewall 3 can be the same in any circumferential position but is in this embodiment increasing towards the opening 6. Essentially the first part 2a of the inner bottom 2 may comprise a surface area being parallel to the first lower surface 10a of the base 10 and the second part 2b of the inner bottom 2 may comprise a surface area being parallel to the second lower surface 10b of the base 10.

FIG. 4 shows an annular wrist support 14 surrounding the bowl 1 facilitating the handling of the bowl 1 in the first position. The wrist support may have a recess underneath the opening 6 of the bowl 1 in order to facilitate that this opening may be lowered and moved into the recess when inclining the bowl from the first into the second stable position.

After transferring the graft into the transport device 12, the transport device 12 may be detached from the connector 11, for example a Luer-lock. The graft in the transport device 12 may be transported to direct surgery or longer storage. For this purpose the transport device 12 may be hermetically closable, preferably re-openable prior to surgery.

Preferably, as shown in FIG. 6 the transport device 12 is configured to get also attached to the distal end 15b of an applicator 15 for ejecting the graft directly through the applicator 15 into the anterior eye chamber of a patient. FIGS. 6 and 7 show a first possible embodiment of an applicator.

For that purpose in the shown preferred embodiment the applicator 15 is configured at its distal end 15b to get connected to the transportation device 12 and at its proximal end 15a to get inserted into the anterior eye chamber through an incision.

The applicator 15 may furthermore comprise a guiding element 15c being situated in the tube of the applicator and extending out of the tube of the applicator 15 beyond its outlet opening 15d. This guiding element 15c is shown in more detail in the views of FIG. 7, particularly the cross sectional view.

Such applicator 15 is disclosed as a device for the transplantation of a Descemet's membrane-endothelium graft in applicants own patent application EP 19161116.9

As far as admissible by national law the disclosure of EP 19161116.9 is incorporated by reference.

In addition FIG. 8 and FIG. 9 show the possibility to connect the transport device 12 to a second embodiment of an applicator 15, the applicator essentially being formed as a tube having a connector at its distal end for connecting to the transport device 12, the tube being tapered and flattened towards the ejection opening at the distal end 15a. The applicator 15 of FIGS. 8 and 9 does not have a guiding element.

The invention claimed is:

1. Device for the preparation of a Descemet's membrane-endothelium graft comprising
   a. a bowl with an inner bottom and a sidewall surrounding the inner bottom, the bowl being configured to receive a fluid and a Descemet's membrane-endothelium graft or a donor cornea graft comprising a Descemet's membrane-endothelium graft floating in the fluid,
   b. a preparation area located in a first part of the inner bottom, the preparation area being configured for receiving and preparing the graft prior to transport, and
   c. a transfer area located in a second part of the inner bottom between the preparation area and an outlet opening in the sidewall, the outlet opening being entirely located below an upper rim of the sidewall, wherein
   the bowl comprises a base configured for placing the bowl on a support, the base being configured to provide a first stable position of the bowl for preparing the graft and a second stable position of the bowl for transferring the prepared graft towards the outlet opening, and
   in the second stable position the bowl is displaced from the first stable position by an angle of rotation about a horizontal axis so that in the second stable position a height of the outlet opening is lower than in the first stable position.

2. The device according to claim 1, wherein the transfer area is increasing in height towards the outlet opening in the first stable position of the bowl.

3. The device according to claim 1, further comprising a transport device, and wherein the outlet opening in the sidewall leads into a connector to which the transport device is at least temporarily attachable, the transport device being configured to receive the prepared graft for transport purposes.

4. The device according to claim 3, wherein the outlet opening, the connector and/or the attached transport device is positioned higher than the preparation area at least in the first stable position of the bowl.

5. The device according to claim 3, further comprising an applicator configured to eject the graft, and wherein the transport device is configured to be connected to the applicator after transport to the applicator.

6. The device according to claim 1, wherein a height of the sidewall above the inner bottom is constant throughout or increasing toward the outlet opening.

7. The device according to claim 1, wherein the first part of the inner bottom comprises a first plane surface area surrounding the preparation area and the second part of the inner bottom comprises a second plane surface area which is a part of the transfer area, the second plane surface area rising in height towards the outlet opening at least in the first stable position of the bowl.

8. The device according to claim 7, wherein in a top view of the bowl the second surface part is tapered towards the outlet opening.

9. The device according to claim 8, wherein the tapered second surface part forms a funnel, the first surface part being at least partially circular.

10. Device for the preparation of a Descemet's membrane-endothelium graft comprising
    a. a bowl with an inner bottom and a sidewall surrounding the inner bottom, the bowl being configured to receive a fluid and a Descemet's membrane-endothelium graft or a donor cornea graft comprising a Descemet's membrane-endothelium graft floating in the fluid,
    b. a preparation area located in a first part of the inner bottom, the preparation area being configured for receiving and preparing the graft prior to transport, and
    c. a transfer area located in a second part of the inner bottom between the preparation area and an outlet opening in the sidewall, the outlet opening being entirely located below an upper rim of the sidewall, wherein
    the bowl comprises a base configured for placing the bowl on a support, the base being configured to provide a first stable position of the bowl for preparing the graft and a second stable position of the bowl for transferring the prepared graft towards the outlet opening and the preparation area comprises a recess, an inner surface of the recess being located below an area of the inner bottom surrounding the recess.

11. The device according to claim 10, wherein the inner surface of the recess further comprises at least one opening, the at least one opening being in fluid connection with a channel in the bowl configured for extracting fluid out of the recess.

12. The device according to claim 11, wherein the at least one opening comprises a plurality of openings.

13. The device according to claim 11, wherein the inner surface of the recess further comprises at least one opening, the at least one opening being in fluid connection with a channel in the bowl configured for extracting fluid out of the recess.

14. The device according to claim 13, wherein the preparation area is formed by a separate bottom element configured to be insertable into the inner bottom and removable out of the inner bottom.

15. The device according to claim 14, wherein the bowl comprises a hollow chamber underneath the inner bottom and being open towards the inner bottom and configured for receiving the separate bottom element, the channel merging into the hollow chamber.

16. The device according to claim 10, wherein the preparation area is formed by a separate bottom element configured to be insertable into the inner bottom and removable out of the inner bottom.

17. The device according to claim 16, wherein the bowl comprises a hollow chamber underneath the inner bottom, the hollow chamber being open towards the inner bottom and configured for receiving the separate bottom element, the channel merging into the hollow chamber.

18. Device for the preparation of a Descemet's membrane-endothelium graft comprising
    a. a bowl with an inner bottom and a sidewall surrounding the inner bottom, the bowl being configured to receive a fluid and a Descemet's membrane-endothelium graft or a donor cornea graft comprising a Descemet's membrane-endothelium graft floating in the fluid, b. a preparation area located in a first part of the inner bottom, the preparation area being configured for receiving and preparing the graft prior to transport, and
c. a transfer area located in a second part of the inner bottom between the preparation area and an outlet opening in the sidewall, the outlet opening being entirely located below an upper rim of the sidewall, wherein
the bowl comprises a base configured for placing the bowl on a support, the base being configured to provide a first stable position of the bowl for preparing the graft and a second stable position of the bowl for transferring the prepared graft towards the outlet opening and the upper rim of the sidewall surrounding the transfer area is increasing in height towards the outlet opening at least in the first stable position of the bowl.

19. Device for the preparation of a Descemet's membrane-endothelium graft comprising
   a. a bowl with an inner bottom and a sidewall surrounding the inner bottom, the bowl being configured to receive a fluid and a Descemet's membrane-endothelium graft or a donor cornea graft comprising a Descemet's membrane-endothelium graft floating in the fluid,
   b. a preparation area located in a first part of the inner bottom, the preparation area being configured for receiving and preparing the graft prior to transport, and
   c. a transfer area located in a second part of the inner bottom between the preparation area and an outlet opening in the sidewall, the outlet opening being entirely located below an upper rim of the sidewall, wherein
   the bowl comprises a base configured for placing the bowl on a support, the base being configured to provide a first stable position of the bowl for preparing the graft and a second stable position of the bowl for transferring the prepared graft towards the outlet opening and a lower surface of the base comprises
      a. a plane first lower surface part underneath the preparation area and a plane second lower surface part underneath the transfer area, the second lower surface area rising in height in a direction towards the outlet opening, or
      b. a first lower surface part underneath the preparation area having a first set of at least three contact elements and a second lower surface part underneath the transfer area having a second set of at least three contact elements, tips of the first set of contact elements being located in a first plane and tips of the second set of contact elements being located in a second plane, the second plane rising in height in a direction towards the outlet opening.

20. The device according to claim 19, wherein the lower surface of the base is configured so that in the first stable position the bowl is positioned on a support with the plane first lower surface part or the contact elements of the first lower surface part contacting the support and in the second stable position the bowl is positioned on the support with only the plane second lower surface part or the contact elements of the second lower surface part contacting the support.

21. Device for the preparation of a Descemet's membrane-endothelium graft comprising
   a. a bowl with an inner bottom and a sidewall surrounding the inner bottom, the bowl being configured to receive a fluid and a Descemet's membrane-endothelium graft or a donor cornea graft comprising a Descemet's membrane-endothelium graft floating in the fluid,
   b. a preparation area located in a first part of the inner bottom, the preparation area being configured for receiving and preparing the graft prior to transport, and
   c. a transfer area located in a second part of the inner bottom between the preparation area and an outlet opening in the sidewall, the outlet opening being entirely located below an upper rim of the sidewall, wherein
   the bowl comprises a base configured for placing the bowl on a support, the base being configured to provide a first stable position of the bowl for preparing the graft and a second stable position of the bowl for transferring the prepared graft towards the outlet opening and the device further comprising a wrist support shaped as a ring or frame being open in a single circumferential position, the wrist support being configured for receiving the bowl in the first stable position.

* * * * *